(12) United States Patent
Lu

(10) Patent No.: US 12,350,376 B2
(45) Date of Patent: Jul. 8, 2025

(54) LYOPHILIZED POWDER OF LATAMOXEF SODIUM FOR INJECTION AND LYOPHILIZATION METHOD THEREOF

(71) Applicant: Hainan Hailing Chemipharma Corporation Ltd., Haikou (CN)

(72) Inventor: Yifeng Lu, Haikou (CN)

(73) Assignee: HAINAN HAILING CHEMIPHARMA CORPORATION LTD., Haikou (CN)

( * ) Notice: Subject to any disclaimer, the term of this patent is extended or adjusted under 35 U.S.C. 154(b) by 688 days.

(21) Appl. No.: 17/564,268

(22) Filed: Dec. 29, 2021

(65) Prior Publication Data

US 2022/0304933 A1    Sep. 29, 2022

Related U.S. Application Data

(63) Continuation of application No. PCT/CN2021/134862, filed on Dec. 1, 2021.

(30) Foreign Application Priority Data

Mar. 25, 2021   (CN) .......................... 202110320195.8

(51) Int. Cl.
  *A61K 9/19*       (2006.01)
  *A61K 9/00*       (2006.01)
  *A61K 31/5365*    (2006.01)

(52) U.S. Cl.
  CPC .............. *A61K 9/19* (2013.01); *A61K 9/0019* (2013.01); *A61K 31/5365* (2013.01)

(58) Field of Classification Search
  None
  See application file for complete search history.

(56) References Cited

FOREIGN PATENT DOCUMENTS

CN          110314163 A    * 10/2019   ......... A61K 31/5365

* cited by examiner

*Primary Examiner* — Anna R Falkowitz
*Assistant Examiner* — Edwin Coleman Mitchell

(57) ABSTRACT

A lyophilized powder of latamoxef sodium for injection and a lyophilization method thereof are provided. The lyophilized powder of latamoxef sodium for injection includes the following raw materials by weight: 20~40 parts of latamoxef sodium, 8~15 parts of lyophilized adjuvant, 6~18 parts of excipient and 30~55 parts of water; by optimizing a raw material process thereof, the present disclosure prepares lyophilized adjuvant and performs twice drying, so that the raw material has stable quality, less impurities, high purity, less adverse reactions and high efficacy; at the same time, the preparation process is innovated and improved to reduce a preparation temperature and ensure stable quality of a drug solution.

6 Claims, No Drawings

LYOPHILIZED POWDER OF LATAMOXEF SODIUM FOR INJECTION AND LYOPHILIZATION METHOD THEREOF

BACKGROUND

1. Technical Field

The present disclosure generally relates to the field of drug preparation, and especially relates to a lyophilized powder of latamoxef sodium for injection and a lyophilization method thereof.

2. Description of Related Art

Latamoxef sodium for injection is suitable for various infections caused by sensitive bacteria, such as sepsis, meningitis, respiratory infection (pneumonia, bronchitis, bronchiectasis, pulmonary suppuration, empyema, etc.), digestive system infection (cholangitis, cholecystitis, etc.), intraperitoneal infection (liver abscess, peritonitis, etc.), urinary and reproductive system infection (nephritis, cystitis, urethritis, gonorrhea, epididymitis, intrauterine infection, uterine adnexitis, pelvic inflammation, etc.), skin and soft tissue infection, bone and joint infection and trauma infection.

At present, excipient used for producing the lyophilized powder of latamoxef sodium for injection is a single mannitol, which has problems of long lyophilization time, a high drying temperature, a high energy consumption and low clarity of a finished product and a lower qualified rate of a solution color, so that high moisture and impurities and unstable quality are occurred in latamoxef sodium for injection that has been obtained by the conventional lyophilization method.

SUMMARY

The technical problems to be solved: in view of the shortcomings of the related art, the present disclosure provides a lyophilized powder of latamoxef sodium for injection and a lyophilization method thereof which can solve the conventional problems above mentioned in the related art.

The technical solution adopted for solving technical problems of the present disclosure is: a lyophilized powder of latamoxef sodium for injection includes the following raw materials by weight: 20~40 parts of latamoxef sodium, 8~15 parts of lyophilized adjuvant, 6~18 parts of excipient and 30~55 parts of water; the lyophilized adjuvant composed of ginkgolide, β-Glucosidase and mannitol; and the excipient selected from one or more of lactose, mannitol, dextran, glycine and glucose.

Wherein the raw materials includes the following parts by weight: 30 parts of latamoxef sodium, 12 parts of lyophilized adjuvant, 12 parts of excipient and 43 parts of water; the lyophilized adjuvant composed of ginkgolide, β-Glucosidase and mannitol, with a weight ratio of 1~3: 0.1~2:0.6~3.9 thereof.

A lyophilization method of latamoxef sodium for injection includes the following step:

step S1, providing a lyophilized powder of latamoxef sodium for injection, lyophilized powder of latamoxef sodium for injection comprising the following raw materials by weight: 20~40 parts of latamoxef sodium, 8~15 parts of lyophilized adjuvant, 6~18 parts of excipient and 30~55 parts of water; the lyophilized adjuvant composed of ginkgolide, β-Glucosidase and mannitol; and the excipient selected from one or more of lactose, mannitol, dextran, glycine and glucose;

step S2, preparing the lyophilized adjuvant: mixing ginkgolide, β-Glucosidase and mannitol in a corresponding proportion, adding 3~5 times volume thereof water to stir, wherein a stirring rate is 600~1200 rpm, a stirring time is 60~150 s, and then placing the above mixture solution at a temperature of −14~−10° C. to obtain the lyophilized adjuvant;

step S3, evenly mixing the above 20~40 parts of latamoxef sodium, 8~15 parts of lyophilized adjuvant, 6~18 parts of excipient and 30~55 parts of water by an oscillator, to obtain a suspension;

step S4, primary drying: placing the suspension on a shelf, slowly raising the temperature to −6~3° C. for performing heat preservation, and continuing to perform heat preservation for 3~5 hours after ice crystals of a product in the primary drying process completely disappear; and step S5, secondary drying: raising the temperature of the suspension that has been dried in the step S3 to 12~15° C. for performing heat preservation of 0.3~1.5 hours, and continuing to raise the temperature of the shelf to 33~37° C., and then performing heat preservation for 3~5 hours after the temperature of the product in the secondary drying reaches 33~37° C.

Wherein a placement time in step S1 is 3~8 hours.

Wherein a heating rate in the step S3 is 0.30~0.35° C./min.

Wherein a heating rate in step S4 is 0.50~0.55° C./min.

Wherein a continuous heating rate in the step S4 is 0.30~0.35° C./min.

The present disclosure provides the advantages as below, compared with the related art:

the present disclosure is provided for a reasonable selection of raw materials and a scientific ratio, the lyophilized adjuvant is selected from ginkgolide, β-Glucosidase and mannitol that are mixed in a proportion and performed auxiliary lyophilization to avoid hydrolysis, oxidation, condensation and fusion in the drying process; by optimizing the raw material process, the raw material has stable quality, less impurities, high purity, less adverse reactions and high efficacy; at the same time, the preparation process is innovated and improved to reduce the preparation temperature and ensure stable quality of the drug solution, the lyophilization method is configured to perform secondary drying to make the moisture, impurities and quality of the finished product more stable.

DETAILED DESCRIPTION

In order to more clearly understand the technical solution hereinafter in embodiments of the present disclosure, reference will now be made in detail to embodiments to further explain the present disclosure.

Unless otherwise specified, experimental methods used in the embodiment of the present disclosure are conventional methods.

The materials and reagents used in the embodiment of the present disclosure can be obtained from commercial sources, unless otherwise specified.

A First Embodiment

A lyophilized powder of latamoxef sodium for injection includes the following raw materials by weight: 20 parts of latamoxef sodium, 8 parts of lyophilized adjuvant, 6 parts of lactose and 30 parts of water. The lyophilized adjuvant is composed of ginkgolide, β-Glucosidase and mannitol, with a weight ratio of 1:0.1:0.6 thereof.

A Second Embodiment

A lyophilized powder of latamoxef sodium for injection includes the following raw materials by weight: 40 parts of latamoxef sodium, 15 parts of lyophilized adjuvant, 18 parts of mannitol and 55 parts of water. The lyophilized adjuvant is composed of ginkgolide, β-Glucosidase and mannitol, with a weight ratio of 3:2:3.9 thereof.

A Third Embodiment

A lyophilized powder of latamoxef sodium for injection includes the following raw materials by weight: 30 parts of latamoxef sodium, 12 parts of lyophilized adjuvant, 12 parts of glycine and 42 parts of water. The lyophilized adjuvant is composed of ginkgolide, β-Glucosidase and mannitol, with a weight ratio of 2:1.2:2.3 thereof.

The lyophilized powder in the first to third embodiments above is prepared according to the following lyophilization method:

step S1, preparing the lyophilized adjuvant: mixing ginkgolide, β-Glucosidase and mannitol composition in a corresponding proportion, adding 3~5 times volume thereof water to stir, wherein a stirring rate is 900 rpm, a stirring time is 120 s, and then placing the above mixture solution at a temperature of −12° C. to obtain the lyophilized adjuvant;

step S2, evenly mixing the above 20~40 parts of latamoxef sodium, 8~15 parts of lyophilized adjuvant, 6~18 parts of excipient and 30~55 parts of water by an oscillator, to obtain a suspension;

step S3, primary drying: placing the suspension on a shelf, slowly raising the temperature to −4° C. at a heating rate of 0.33° C./min for performing heat preservation, and continuing to perform heat preservation for 4 hours after ice crystals of a product in the primary drying process completely disappear; and step S4, secondary drying: raising the temperature of the suspension that has been dried in the step S3 to 13° C. at a heating rate of 0.53° C./min for performing heat preservation of 1 hour, and continuing to raise the temperature of the shelf to 35° C. at a heating rate of 0.33° C./min, and then performing heat preservation for 4 hours after the temperature of the product in the secondary drying reaches 34° C.

A Fourth Embodiment

A difference between the fourth embodiment and the third embodiment is that: a lyophilization method of lyophilized powder of latamoxef sodium for injection includes the following steps:

step S1, preparing the lyophilized adjuvant: mixing ginkgolide, β-Glucosidase and mannitol in a corresponding proportion, adding 3~5 times volume thereof water to stir, wherein a stirring rate is 600 rpm, a stirring time is 60 s, and then placing the above mixture solution at a temperature of −14° C. to obtain the lyophilized adjuvant;

step S2, evenly mixing the above 20~40 parts of latamoxef sodium, 8~15 parts of lyophilized adjuvant, 6~18 parts of excipient and 30~55 parts of water by an oscillator, to obtain a suspension;

step S3, primary drying: placing the suspension on the shelf, slowly raising the temperature to −6° C. at a heating rate of 0.30° C./min for performing heat preservation, and continuing to perform heat preservation for 3 hours after ice crystals of a product in the primary drying process completely disappear; and step S4, secondary drying: raising the temperature of the suspension that has been dried in the step S3 to 12° C. at a heating rate of 0.50° C./min for performing heat preservation of 0.3 hour, and continuing to raise the temperature of the shelf to 33° C. at a heating rate of 0.30° C./min, and then performing heat preservation for 3 hours after the temperature of the product in the secondary drying reaches 33° C.

A Fifth Embodiment

A difference between the fifth embodiment and the third embodiment is that: a lyophilization method of lyophilized powder of latamoxef sodium for injection includes the following steps:

step S1, preparing the lyophilized adjuvant: mixing ginkgolide, β-Glucosidase and mannitol in a corresponding proportion, adding 3~5 times volume thereof water to stir, wherein a stirring rate is 1200 rpm, a stirring time is 150 s, and then placing the above mixture solution at a temperature of −10° C. to obtain the lyophilized adjuvant;

step S2, evenly mixing the above 20~40 parts of latamoxef sodium, 8~15 parts of lyophilized adjuvant, 6~18 parts of excipient and 30~55 parts of water by an oscillator, to obtain a suspension;

step S3, primary drying: placing the suspension on the shelf, slowly raising the temperature to −3° C. at a heating rate of 0.35° C./min for performing heat preservation, and continuing to perform heat preservation for 5 hours after ice crystals of the product in the primary drying process completely disappear; and step S4, secondary drying: raising the temperature of the suspension that has been dried in the step S3 to 15° C. at a heating rate of 0.55° C./min for performing heat preservation of 1.5 hours, and continuing to raise the temperature of the shelf to 37° C. at a heating rate of 0.35° C./min, and then performing heat preservation for 5 hours after the temperature of the product in the secondary drying reaches 37° C.

A Sixth Embodiment

A difference between the sixth embodiment and the third embodiment is that: a lyophilization method of lyophilized powder of latamoxef sodium for injection includes: a heating rate in the step S3 is 0.38° C./min.

A First Comparative Example

A difference between the first comparative example and the third embodiment is that: a lyophilized powder of latamoxef sodium for injection includes: the following raw materials by weight: 50 parts of latamoxef sodium, 20 parts of lyophilized adjuvant, 20 parts of excipient and 25 parts of water.

A Second Comparative Example

A difference between the second comparative example and the third embodiment is that: the lyophilized adjuvant is composed of ginkgolide, 3-Glucosidase and mannitol, with a weight ratio of 4:3:4 thereof.

A Third Comparative Example

A difference between the third comparative example and the third embodiment is that: the lyophilized adjuvant is composed of an equal amount of dextran, β-Glucosidase and mannitol.

1. Stability

According to requirements of Chinese Pharmacopoeia, properties, pH values, contents and total impurities of samples prepared in the first to sixth embodiments and the first to third comparative examples are analyzed below:

|  | Time | Property | pH | Content (%) | total impurity(%) |
|---|---|---|---|---|---|
| First embodiment | 0 day | Off-white loose massive | 6.35 | 99.8 | 0.20 |
|  | One month | Off-white loose massive | 6.42 | 99.6 | 0.21 |
|  | Three months | Off-white loose massive | 6.35 | 99.5 | 0.22 |
| Second embodiment | 0 day | Off-white loose massive | 6.35 | 100.0 | 0.19 |
|  | One month | Off-white loose massive | 6.35 | 99.8 | 0.20 |
|  | Three months | Off-white loose massive | 6.35 | 99.6 | 0.22 |
| Third embodiment | 0 day | Off-white loose massive | 6.35 | 100.0 | 0.10 |
|  | One month | Off-white loose massive | 6.35 | 100.0 | 0.12 |
|  | Three months | Off-white loose massive | 6.35 | 99.9 | 0.14 |
| Fourth embodiment | 0 day | Off-white loose massive | 6.35 | 99.7 | 0.18 |
|  | One month | Off-white loose massive | 6.35 | 99.4 | 0.19 |
|  | Three months | Off-white loose massive | 6.35 | 99.3 | 0.21 |
| Fifth embodiment | 0 day | Off-white loose massive | 6.35 | 99.8 | 0.17 |
|  | One month | Off-white loose massive | 6.35 | 99.7 | 0.19 |
|  | Three months | Off-white loose massive | 6.35 | 99.2 | 0.20 |
| Sixth embodiment | 0 day | Off-white loose massive | 6.35 | 99.7 | 0.19 |
|  | One month | Off-white loose massive | 6.35 | 99.5 | 0.21 |
|  | Three months | Off-white loose massive | 6.35 | 99.4 | 0.23 |
| First comparative example | 0 day | Off-white loose massive | 6.35 | 92.6 | 0.23 |
|  | One month | Creamy loose massive | 6.35 | 90.2 | 0.27 |
|  | Three months | Faint yellow loose massive | 6.35 | 89.6 | 0.28 |
| Second comparative example | 0 day | Off-white loose massive | 6.35 | 90.4 | 0.24 |
|  | One month | Faint yellow loose massive | 6.35 | 89.6 | 0.29 |
|  | Three months | Faint yellow loose massive | 6.35 | 87.3 | 0.31 |
| Third comparative example | 0 day | Off-white loose massive | 6.35 | 90.3 | 0.27 |
|  | One month | Faint yellow loose massive | 6.35 | 87.6 | 0.29 |
|  | Three months | Yellow loose massive | 6.35 | 87.2 | 0.30 |

It can be seen from the above table that the injection of the lyophilized powder prepared by the method is off-white loose massive, a neutral pH value, a high content and low total impurities, the product quality is stable and better relative to other listed products.

Although the features and elements of the present disclosure are described as embodiments in particular combinations, each feature or element can be used alone or in other various combinations within the principles of the present disclosure to the full extent indicated by the broad general meaning of the terms in which the appended claims are expressed.

What is claimed is:

1. A lyophilization method of latamoxef sodium for injection comprising:
    step S1, preparing a lyophilized adjuvant by mixing ginkgolide, β-Glucosidase and mannitol, adding 3-5 times volume thereof water and stirring to obtain a mixture solution, and placing the mixture solution at −14 degrees Celsius (C) to 10° C. to obtain the lyophilized adjuvant,
    wherein a stirring rate thereof is 600-1200 revolutions per minute (rpm) and a stirring time thereof is 60-150 seconds(s);
    step S2, mixing 20-40 parts of latamoxef sodium, 8-15 parts of lyophilized adjuvant, 6-18 parts of excipient and 30-55 parts of water by an oscillator, to obtain a suspension;
    step S3, primary drying by placing the suspension on a shelf, heating the suspension to −6-3° C., performing heat preservation on the suspension at −6-3° C. until ice crystals in the suspension completely disappear to obtain a primary dried mixture, and performing heat preservation on the primary dried mixture for 3-5 hours at −6-3° C. to obtain a secondary dried mixture; and
    step S4, secondary drying by heating the secondary dried mixture to 12-15° C., performing heat preservation on the secondary dried mixture at 12-15° C. for 0.3-1.5 hours to obtain a tertiary dried mixture, then heating the tertiary dried mixture to 33-37° C., and performing heat preservation on the tertiary dried mixture at 33-37° C. for 3-5 hours to obtain a powder of the latamoxef sodium for injection.

2. The lyophilization method of latamoxef sodium for injection as claimed in claim 1, wherein in step S1, the mixture solution is placed at −14° C. to 10° C. for 3-8 hours.

3. The lyophilization method of latamoxef sodium for injection as claimed in claim 1, wherein the heating rate of the suspension in step S3 is 0.30-0.35° C./min.

4. The lyophilization method of latamoxef sodium for injection as claimed in claim 1, wherein the heating rate of the secondary dried mixture in step S4 is 0.50-0.55° C./min.

5. The lyophilization method of latamoxef sodium for injection as claimed in claim 1, wherein the heating rate of the tertiary dried mixture is 0.30-0.35° C./min.

6. The lyophilization method of latamoxef sodium for injection as claimed in claim 1, wherein raw materials of the powder of the latamoxef sodium for injection comprise the following parts by weight: 30 parts of latamoxef sodium, 12 parts of lyophilized adjuvant, 12 parts of excipient and 43 parts of water; the lyophilized adjuvant composed of ginkgolide, β-Glucosidase and mannitol, with a weight ratio of 1-3:0.1-2:0.6-3.9 thereof.

* * * * *